(12) United States Patent
Törmälä et al.

(10) Patent No.: US 6,406,498 B1
(45) Date of Patent: Jun. 18, 2002

(54) BIOACTIVE, BIOABSORBABLE SURGICAL COMPOSITE MATERIAL

(75) Inventors: Pertti Törmälä; Tero Välimaa; Henna Niiranen; Timo Pohjonen, all of Tampere; Penti Rokkanen, Helsinki, all of (FI)

(73) Assignee: Bionx Implants Oy, Tampere (FI)

( * ) Notice: Subject to any disclaimer, the term of this patent is extended or adjusted under 35 U.S.C. 154(b) by 0 days.

(21) Appl. No.: 09/148,838

(22) Filed: Sep. 4, 1998

(51) Int. Cl.$^7$ .................................................. A61F 2/36
(52) U.S. Cl. .................................. 623/23.75; 623/11.11
(58) Field of Search ............................. 606/53; 623/11, 623/11.11, 23.75, 23.58, 23.61; 424/423, 424

(56) References Cited

U.S. PATENT DOCUMENTS

| | | |
|---|---|---|
| 4,539,256 A | 9/1985 | Shipman |
| 4,612,923 A | 9/1986 | Kronenthal |
| 4,655,203 A | 4/1987 | Törmälä et al. |
| 4,655,777 A * | 4/1987 | Dunn et al. .................... 623/16 |
| 4,743,257 A | 5/1988 | Törmälä et al. |
| 4,863,472 A | 9/1989 | Törmälä et al. |
| 4,898,186 A | 2/1990 | Ikada et al. |
| 4,968,317 A | 11/1990 | Törmälä et al. |
| 5,084,051 A | 1/1992 | Törmälä et al. |
| 5,502,092 A * | 3/1996 | Barrows et al. ............... 521/64 |
| 5,562,704 A | 10/1996 | Tamminmäki et al. |
| 5,569,250 A | 10/1996 | Sarver et al. |
| 5,674,286 A * | 10/1997 | D'Alessio et al. ........ 623/11.11 |
| 5,700,477 A * | 12/1997 | Rosenthal et al. ........... 424/426 |
| 5,782,789 A * | 7/1998 | Herweck et al. .............. 602/52 |
| 6,013,853 A * | 1/2000 | Athanasiou et al. ..... 623/23.75 |

FOREIGN PATENT DOCUMENTS

| | | |
|---|---|---|
| EP | 0146398 | 6/1985 |
| EP | 423155 | 4/1991 |
| EP | 0442911 | 8/1991 |
| EP | 449 867 | 10/1991 |
| EP | 0795336 A1 | 9/1997 |
| EP | 0933089 A2 | 8/1999 |
| FI | 88111 | 12/1992 |
| FI | 98136 | 1/1997 |
| FI | 965111 | 1/1997 |
| FI | 952884 | 2/1997 |
| FI | 955547 | 12/1997 |
| WO | WO 90/04982 | 5/1990 |
| WO | WO 96/21628 | 7/1996 |
| WO | WO 96/41596 | 12/1996 |
| WO | WO 97/11725 | 4/1997 |

OTHER PUBLICATIONS

Niiranen et al., "Self–Reinforced Bioactive Glass–Bioabsorbable Polymer Composites", Mat. Res. Soc. Symp. Proc., vol. 550, 1999.

Modern Plastics, Guide to Plastics, 1987, McGraw–Hill, New York, pp. 152–153 and Modern Plastics Encyclopedia, Mid–Oct. Issue 1989, McGraw–Hill, New York, 1989, pp. 600, 606–607, 608–609, 614.

D. McGuire, et al., American Academy of Orthopaedic Surgeons, New Orleans, 65$^{th}$ Annual Meeting, Mar. 19–23, 1998, Final Program, p. 261.

S.I. Ertel et al., J. Biomed. Mater. Res., 29 (1995) 1337–1348, and P. Tormala et al., Proc. Instn. Mech. Engrs Part H, 212 (1998) 101–111.

N. Inoue, in Hydrostatic Extrusion, N. Inoue and M. Nishihara (eds), Elsevier Applied Science Publishers, Barbing, England, 1985, p. 333–362.

M. Brink et al., Bioceramics, 9, 1996, pp. 127–130.

T. Kokubo et al. In Bioceramics, vol. 2, ed. G. Heimke, Deutsche Keramische Gesellschaft e. V., Cologne, Germany, 1990 pp. 235–242.

Maracolongo et al., J. Biomed. Mater. Res., 39 (1998) pp. 161–170.

M. Manninen and T. Pohjonen, Biomaterials, 14 (1993) 305–312.

* cited by examiner

*Primary Examiner*—Gene Mancene
*Assistant Examiner*—Eduardo C. Robert
(74) *Attorney, Agent, or Firm*—Kenyon & Kenyon

(57) ABSTRACT

The Applicants' invention is a bioactive, biocompatible, bioabsorbable surgical composite that is fabricated bioabsorbable polymers, copolymers or polymer alloys that are self-reinforced and contain ceramic particles or reinforcement fibers, and also can be porous. The composite of the invention can be formed into devices like pins, screws, plates, tacks, bolts, intramedullary nails, suture anchors, staples, and many other devices, all of which are useful in bone-to-bone, soft tissue-to-bone or soft tissue-to-soft tissue fixation or in fixation of bioabsorbable and/or biostable implants in or on bone or soft tissue.

10 Claims, 9 Drawing Sheets

BIOACTIVE, BIOABSORBABLE SURGICAL COMPOSITE MATERIAL

The invention relates to bioactive, biocompatible, bioabsorbable surgical composites and devices, such as pins, screws, plates, tacks, bolts, intramedullary nails, suture anchors, staples, or other devices which are applied in bone-to-bone, soft tissue-to-bone or soft tissue-to-soft tissue fixation or in fixation of bioabsorbable and/or biostable implants in, and/or on, bone or soft tissue, which composites and devices are fabricated of bioabsorbable polymers, copolymers or polymer alloys that are self-reinforced and contain ceramic particles or reinforcement fibers and porosity.

BACKGROUND OF THE INVENTION

Bioabsorbable surgical devices such as, e.g., pins, screws, plates, tacks, bolts, intramedullary nails, suture anchors, or staples, etc., made from bioabsorbable polymers are becoming more frequently used in the medical profession in bone-to-bone, soft tissue-to-bone or soft tissue-to-soft tissue fixation. Numerous publications describe the aforementioned and other bioabsorbable devices for such tissue fixation applications, e.g., U.S. Pat. No. 4,655,203, U.S. Pat. No. 4,743,257, U.S. Pat. No. 4,863,472, U.S. Pat. No. 5,084,051, U.S. Pat. No 4,968,317, EPO Pat. No. 449,867, U.S. Pat. No. 5,562,704, PCT/FI 96/00351, PCT/FI 96/00511, FI Pat. Appl. No. 965111, U.S. Pat. appl. Ser. No. 08/873,174, U.S. Pat. appl. Ser. No. 08/887,130, U.S. Pat. appl. Ser. No. 08/914,137, and U.S. Pat. appl. Ser. No. 08/921,533, the entire respective disclosures of which are incorporated herein by way of this reference.

Surgeons would prefer to use bioabsorbable devices that eventually resorb and disappear from the body after they have served their purpose during tissue fixation and healing and, accordingly, are not needed any more. However, a device made from bioabsorbable polymer must have sufficient strength and stiffness for effective tissue fixation and it must retain sufficient strength to perform its function during the tissue healing process, before it eventually is absorbed by the body. It is advantageous to mix different additives into bioabsorbable polymers to modify their properties and to yield devices having useful properties. Such typical additives include ceramic, which optionally can be bioactive, particle fillers and short fiber reinforcements (having fiber lengths typically between 1 $\mu$m–10 mm), each of which can promote osteoconductivity of bioabsorbable bone fracture fixation devices, such as pins, screws or plates or other fixation implants like suture anchors and tacks, which are in contact with bone tissue.

Bioactive, bioabsorbable ceramic fillers and fibers and/or their use in bioabsorbable devices as bioactive ceramic fillers and/or reinforcements have been described in several of the aforementioned publications, and also are describe in, e.g., EPO Pat. Appl. 0 146 398, U.S. Pat. No. 4,612,923, and PCT Pat. Appl. WO 96/21628, the entire disclosures of each of which are incorporated herein by way of this reference.

Ceramic particle fillers and/or short fiber reinforcements typically are first dry blended with bioabsorbable polymer powder, granulate or flakes, and the mixture is then melt blended in an extruder, injection molding machine or in a compression molding machine. The melt blended extrudate can be pelletized or cooled and crushed and sieved to the desired grain size. Such pellets or grains can be further melt processed, e.g., by extrusion, injection molding or compression molding, into bioabsorbable preforms or they can be used as masterbatches and mixed with nonblended bioabsorbable polymers and melt processed into bioabsorbable preforms which can be processed further mechanically and/or thermomechanically to make surgical devices. It also is possible to melt process many devices directly from pellets or grains or masterbatches of polymer mixtures, e.g., with extrusion, injection molding or compression molding.

Particles or short fibers of bioactive glass, such as are described in PCT Pat. Appl. WO 96/21628, the entire disclosure of which is incorporated herein by way of this reference, are especially advantageous ceramic fillers and/or reinforcements in bioabsorbable polymers because they slowly dissolve under tissue conditions and form hydroxyapatite precipitations, (see, e.g., M. Brink, "Bioactive glasses with a large working range", Doctoral Thesis, Åbo Akademi University, Turku, Finland, 1997, the entire disclosure of which is incorporated herein by way of this reference), which enhances the bone growth in contact with the surface of the device.

However, the surface of melt-molded bioabsorbable polymer composites containing bioactive glass filler and/or fiber reinforcements is coated with a "skin" of bioabsorbable polymer which prevents the immediate direct contact of glass particles with the surrounding tissues and tissue fluids when the melt molded device has been implanted into living tissue. The advantageous direct contact of bioactive glass particles with the tissue environment can develop only weeks or months after implantation when biodegradation of the polymeric surface layer (skin) has proceeded so far that cracks or crazes have developed in the surface layer of composite. Therefore, it is necessary to machine the surfaces of such melt molded composites mechanically to remove the isolating skin layer if immediate contact between glass particles (filler or fibers) is desired. Such a surface machining is, however, time consuming process.

An additional general problem with ceramic particle filled thermoplastic polymer composites is their brittleness, because addition of ceramic fillers into the polymer matrix changes most thermoplastic polymers from tough and ductile to brittle in nature. This is evidenced by significant reduction of both elongation at break and impact strength (see, e.g., Modern Plastics, Guide to Plastics, 1987, McGraw-Hill, N.Y., pp. 152–153 and Modern Plastics Encyclopedia, Mid-October Issue 1989, McGraw-Hill, N.Y., 1989, pp. 600, 606–607, 608–609, 614, the entire disclosures of both of which are incorporated herein by way of this reference). Moreover, even non-filled bioabsorbable thermoplastic polymer devices, which are manufactured by melt molding, may be brittle in their mechanical behavior. That brittleness can be a severe limitation on bioabsorbable devices, leading to premature breaking or to other adverse behavior (see, e.g., D. McGuire, et al., American Academy of Orthopaedic Surgeons, New Orleans, 65th Annual Meeting, Mar. 19–23, 1998, Final Program, p. 261, the entire disclosure of which is incorporated herein by way of this reference). Just as in nonbioabsorbable thermoplastic polymers, ceramic fillers also increase the brittleness of bioabsorbable polymers (see, e.g., Example 1 of this application).

Additionally, the prior art bioabsorbable, particle filled or short fiber filled composites and devices made of them must have low porosities, because porosity weakens the composite and increases its brittleness. However, porosity also provides advantages to an implant which is in contact with bone or other tissue, because (bone) tissue can grow into the pores, accelerating new tissue (bone) formation and locking the implant into contact with the tissue (bone), thereby preventing implant migration. Such surface porosity also would facilitate the contact between the growing bone and ceramic particle or fiber fillers, if the ceramic particles or fibers are at least partially exposed into the pores.

It would, therefore, be advantageous to have a strong and tough (nonbrittle), bioabsorbable composite comprising: (a) a matrix of a bioabsorbable polymer, copolymer (consisting of two or more monomer components) or polymer blend, which matrix is oriented and/or self-reinforced; (b) bioabsorbable, bioactive ceramic particles and/or short fiber filler or reinforcement dispersed in the polymer matrix; (c) pores which are dispersed in the polymer matrix and isolated or at least partially connected with one another, and into which pores at least some free surfaces of the particles or fibers are exposed; and (d) an outer surface comprising a polymer matrix, pores and ceramic particles and/or short reinforcing fibers, wherein a substantial amount of the ceramic particles or fibers have at least one free surface not covered by the polymer's skin.

It would further be advantageous to have surgical implants manufactured of the composite described above, e.g., pins, screws, plates, tacks, bolts, intramedullary nails, suture anchors, staples, or other devices which can be applied in bone-to-bone, soft tissue-to-bone or soft tissue-to-soft tissue fixation or in fixation of bioabsorbable and/or biostable implants in and/or on bone or soft tissue. It also would be advantageous to have such surgical implants manufactured of the composites described above, which implants have pores and bioactive ceramic particles and/or short reinforcement fibers (fillers) that are in direct contact with the bone or tissue to which the implant is applied.

BRIEF SUMMARY OF THE INVENTION

The invention is surgical bioabsorbable composites and devices comprising:
(a) a strong and tough (non-brittle) bioabsorbable polymeric matrix which is oriented and/or self-reinforced;
(b) a bioabsorbable and/or bioactive particle and/or short fiber filler or reinforcement phase dispersed in the polymer matrix;
(c) pores dispersed in the polymer matrix, which pores include particles or short fiber fillers with at least one surface exposed into the pore space; and
(d) an outer surface, wherein the polymer matrix, pores and particles or short fiber fillers therein are at least partially in direct contact with their environment.

DETAILED DESCRIPTION OF THE INVENTION

Figure 1:
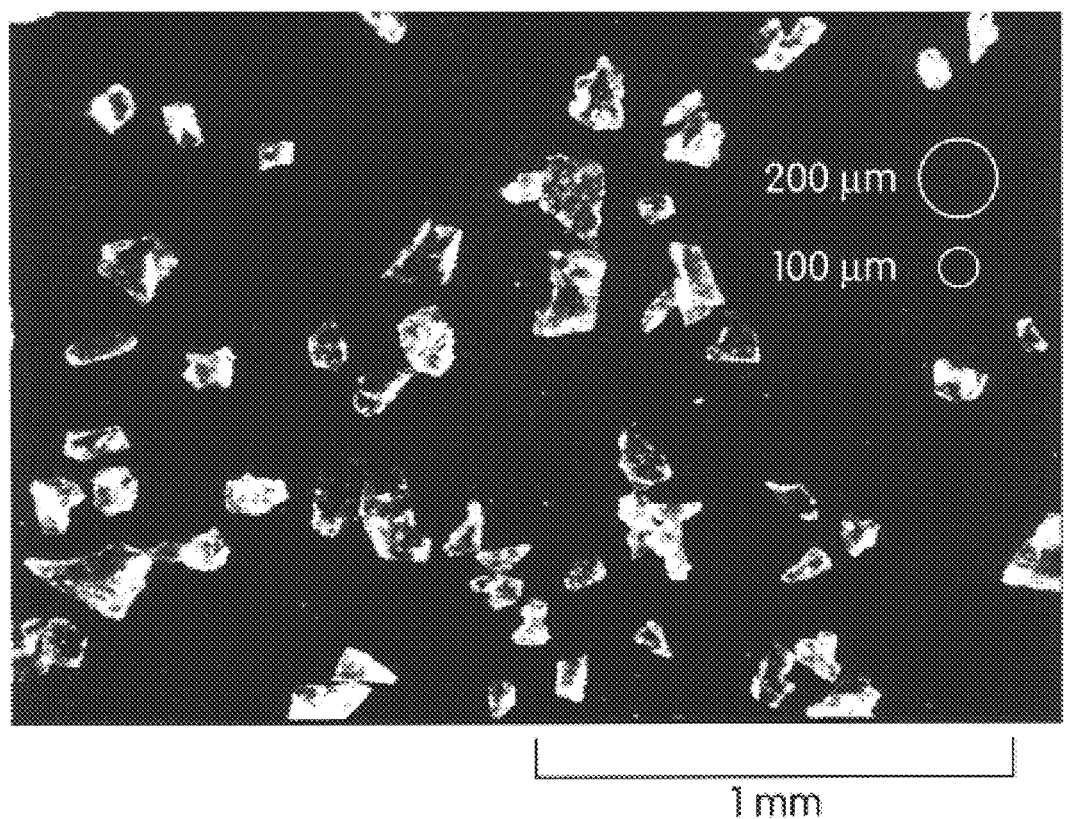
FIG. 1 is a scanning electron microscope (SEM) figure of particles of glass 13-93 (as used herein either "BG-13" or BG 13-93," and containing the following: $Na_2O$—6 wt. %; $K_2O$—12 wt. %; MgO—5 wt. %; CaO—20 wt. %; $P_2O_5$—4 wt. %; and $SiO_2$—53 wt-%) sieved to the particle fraction 50–125 μm.

The biopolymers employed in this invention are synthetic bioabsorbable polymers, copolymers and/or polymer alloys. Such polymers, like those made of poly-α-hydroxy acids and other aliphatic bioabsorbable polyesters, polyanhydrides, polyorthoesters, polyorganophosphatzenes, tyrosine polycarbonates and other bioabsorbable polymers are disclosed in several references mentioned above and also in many other publications, e.g., in U.S. pat. appl. Ser. No. 09/053, 670, U.S. pat. appl. Ser. No. 09/036,259, U.S. pat. appl. Ser. No. 091033,475, U.S. pat. appl. Ser. No. 09/055, 005, U.S. pat. appl. Ser. No. 08/997,458, U.S. pat. appl. Ser. No. 09/054,672, S. Vainionpää et al., Prog. Polym. Sci., 14 (1989) 679–716, FI Pat. No. 952884, FI Pat. No. 955547, WO-90/04982, EP 0449867 B1, U.S. Pat. No. 5,569,250, S. I. Ertel et al., J. Biomed. Mater. Res., 29 (1995) 1337–1348, and P. Törmälä et al., Proc. Instn. Mech. Engrs Part H, 212 (1998) 101–111, the entire disclosures of each of which are incorporated herein by way of this reference.

The absorbable bioactive glasses employed in the invention can be based on $P_2O_5$ as the network former, as in glasses described in U.S. Pat. No. 4,612,923 and in prior art publications mentioned therein, the entire disclosures of each of which are incorporated herein by way of this reference. Such glasses typically can contain additionally at least one alkali or alkaline earth metal oxide, such as sodium oxide, potassium oxide, calcium oxide, magnesium oxide, and the like. Although the custom in the art is to refer to the constituents in the form of the oxides, the oxides per se need not be used in producing the glass. For instance, the following materials also can be used: $(NH_4)_3PO_4$, (NH4) $2HPO_4$, $NaH_2PO_4$, $KH_2PO_4$, $CaCO_3$, $Ca(H_2PO_4)_2$, $MgCO_3$, $P_2O_5$ $MgHPO_4$, $Zn_3(PO_4)_2$, and MgO. As a general rule, the solubility rate (in aqueous media) is increased by increasing the proportion of alkali metal oxides (e.g.,. $Na_2O$ and $K_2O$), and is decreased by increasing the proportion of alkaline earth metal oxides (e.g., CaO and MgO). Thus, within certain limits, the solubility rate of the glass can be varied. Other oxides also can be added, in small amounts, if desired. For example, small amounts of $SiO_2$, $B_2O_3$, and/or ZnO can be added for the purpose of retarding the dissolution rate for certain applications, or for enhancing processability.

Bioactive glasses and glass-ceramics, like those described in the Doctoral Thesis of M. Brink (see supra) and in references therein on pages 9–10 and as described by M. Marcolongo et al. (J. Biomed. Mater. Res., 39 (1998) 161–170, the entire disclosure of which is incorporated herein by reference) can be employed in this invention. Naturally, the invention is not limited to those bioactive, bioabsorbable glasses described herein, but also other glasses can be used in this invention.

Suitable glasses are produced by fusing the ingredients in the desired proportions in a platinum or a dense alumina crucible. Typical fusion temperatures are 800° to 1400° C., and typical fusion times are about one to four hours. After fusion, the molten glass may be quenched, and then subjected to pulverizing to reduce the glass to a very fine particle size. The pulverizing of the glass can be done by known procedures such as air jet milling, ball milling, or the like. Typically, the powders used are of very fine particle size, e.g., below 200 mesh and in some cases below 400 mesh (Tyler Standard Sieve Series). It is also within the scope of the invention to employ the glass in the form of fibers (preferably as short fibers, e.g., fibers having diameters of from about 2 to 200 microns and aspect ratios [length/diameter] of about 1 to 100). The fibers can be made by known methods such as melt spinning.

The proportion of glass filler and/or reinforcement in the polymer can vary from case to case, but will usually be within the range of from about 10 to about 60 weight per cent (wt-%), based on the weight of the filled polymer. In any event, the exact proportion of glass filler is not narrowly critical. The glass is employed in an amount sufficient to increase the bioactivity of the composite.

The glass is incorporated in the polymer matrix by conventional procedures for adding fillers or short fibers to polymers. For instance, polymer pellets and glass powder or fibers, are intimately mixed in a blender, and the mixture is then compounded through an extruder. Injection or compression molding techniques can also be used. The glass can also be used in the form of continuous filaments, and rods comprising the continuous filament glass embedded in a matrix of absorbable polymer can be produced by the extrusion technique known as "pultrusion," wherein the polymer is continuously extruded around glass filaments that are pulled through the extruder nozzle. Such rods can then be granulated (chopped or cut to any desired length, after the pultrusion operation) for further use in manufacturing short fiber reinforced preforms or devices by compression molding, extrusion or injection molding. Such preforms can then be oriented and/or self-reinforced with solid state deformation, like with free or die drawing, biaxial drawing, compression, hydrostatic extrusion or ram extrusion as combined with drawing.

Orientation and/or self-reinforcing techniques, which can be applied to manufacture the materials of the invention have been described in many publications, like in U.S. Pat. No. 4,968,317, EPO Pat. No. 0 423 155, EPO Pat. No. 0 442 911, FI Pat. No. 881 11, FI Pat. No. 98136, U.S. pat. appl. Ser. No. 09/036,259, U.S. Pat. No. 4,898,186, and in U.S. pat. appl. Ser. No. 09/036,259, the entire disclosures of which are incorporated herein by way of this reference.

In this invention we have found surprisingly that by applying drawing-, compression- or shear-type solid state orientation and/or self-reinforcing to bioabsorbable polymeric composites that include bioactive, bioabsorbable ceramic filler and/or short fiber reinforcement, it is possible to manufacture oriented and/or self-reinforced composites which are:

strong and tough;

bioactive (e.g., enhance new bone formation);

porous; and have pores and partially exposed filler particles and/or short fibers on their outer surface.

The new composites of the invention, when used as surgical implants or as components thereof enhance new bone formation both in their surroundings and into the pores of the implant, leading to more rapid healing and fixation of the device than in prior art devices.

Surgical devices made from the composites of the invention, like pins, rods, intramedullary nails, screws, tacks, bolts, tissue and suture anchors, plates, meshes, fibers, threads, cords, felts, fabrics, scaffolds, membranes, etc., can be applied as temporary fixation implants in bone-to-bone, soft tissue-to-bone and soft tissue-to-soft tissue fixation, and also in tissue augmentation procedures and in guided tissue regeneration.

Implants in accordance with the invention can be manufactured of bioabsorbable polymers by using one polymer or a polymer alloy. The implants also can be reinforced additionally by fibers manufactured of a resorbable polymer or of a polymer alloy, or with other biodegradable glass fibers, or ceramic fibers, such as $\beta$-tricalsiumphosphate fibers, bio-glass fibers or CaM fibers (see, e.g., EP146398). Other ceramic particles (like tricalciumphosphate powders) also can be used instead of bioactive glass particles as fillers in implants of the invention, to promote new bone formation.

Implants according to the invention can also contain layered parts comprising, e.g., (a) a flexible outer layer as a surface layer improving the toughness and/or operating as the hydrolysis barrier and (b) a stiff inner layer.

It is natural that the materials and implants of the invention can also contain various additives for facilitating the processability of the material (e.g., stabilizers, antioxidants or plasticizers) or for changing its properties (e.g., plasticizers or ceramic powder materials or biostable fibers, such as carbon) or for facilitating its treatment (e.g., colorants). According to one advantageous embodiment of the invention, the composite also contains other bioactive agent or agents, such as antibiotics, chemotherapeutic agents, agents activating healing of wounds, growth factor(s), bone morphogenic protein(s), anticoagulants (such as heparin), etc. Such bioactive implants are particularly advantageous in clinical use, because they have, in addition to their mechanical effect and bone growth stimulating effects, other biochemical, medical and other effects to facilitate tissue healing and/or regeneration.

A typical manufacturing procedure to make devices of the present invention is as follows:

First the polymer raw material and filler(s) and/or reinforcing fibers and optional additives in the form of a powder, flakes, pellets or granulate, etc., are melted with a continuous process, like extrusion, or with a noncontinuous process, like injection molding or compression molding. The melted material is cooled so that it solidifies to an amorphous or partially crystalline (crystallinity typically 5–50%) preform, like a cylindrical rod or bar, a flat balk with a rectangular cross-section, a plate or a sheet stock. Cooling can be done inside a mold when using injection molding or compression molding techniques. In extrusion, the preform is formed from the material melt in a die, and the preform is then passed onto a cooling belt or into a cooling solution to make a solid preform.

Thereafter, the solid preform is oriented and/or self-reinforced with an uni- and/or biaxial solid state deformation process to create an oriented preform. The self-reinforcing or orientation transforms the preform stock into a strong, tough and partially porous form. The orientation is typically accomplished at a temperature (T) above the $T_g$ (the glass transition temperature) of the polymeric raw material, but below the melting temperature of the material, if it is partially crystalline, and the orientation is typically made by drawing the unoriented preform in the solid state. The drawing can be done freely by fixing the ends of the preform into fixing clamps of a drawing machine, tempering the system to the desired drawing temperature, and increasing the distance between the fixing clamps so that the preform is stretched and oriented structurally. This type of orientation is mainly uniaxial. The drawing can be done also through a conical die, which can have, e.g., a circular, an ellipsoidal, a square, a star-like or rectangular cross-section. When the cross-sectional area of the bioabsorbable polymer billet, which will be drawn through the die, is bigger than the cross-sectional area of the die outlet, the billet is deformed and oriented uni- and/or biaxially during drawing, depending on the geometry of billet and die.

In addition to drawing, pushing deformation can also be applied to the billet. For example, the billet may be forced through the die by drawing and at the same time by pushing the billet mechanically with a piston through the die (ram extrusion) or by pushing the billet through the die with hydrostatic pressure (see, e.g., N. Inoue, in Hydrostatic Extrusion, N. Inoue and M. Nishihara (eds.), Elsevier Applied Science Publishers, Barbing, England, 1985, p. 333–362, the entire disclosure of which is incorporated herein by way of this reference).

It also is possible to create orientation by shearing the flat billet between two flat plates which glide in relation to each other and approach each other at the same time, as is described in U.S. pat. appl. Ser. No. 09/036,259. It also is possible to deform the billet in a compression molding device between flat plates which are pushed towards each other so that the billet deforms biaxially between the plates and attains the desired final thickness. The deformation can be done also by rolling the rod-like or plate-like preform between rollers, which flatten the preform to the desired thickness orienting the material at the same time biaxially. The rolling can be combined with drawing, e.g., by using two pairs of rollers positioned one pair after the other, which rollers have different rolling speeds. The billet and/or die, compression plates or rolls can be heated to the desired deformation temperature with electrical heating or with a suitable heating medium, like a gas or heating liquid. The heating can be done also with microwaves or ultrasonically to accelerate the heating of the billet. Regardless of the deformation method, the purpose of the solid state deformation is the orientation of the material uni- and/or biaxially so that the material is transformed into a strong and ductile one and porosity is created around the filler and/or reinforcement particles, spheres or fibers, thus enhancing the interaction of filler and/or reinforcement with its environment.

Following the orientation step, surgical devices can be formed from the oriented preforms by machining, stamping, thermoforming or with other mechanical, thermal or thermomechanical methods. After finishing, cleaning and drying, the surgical devices of the invention can be packed into a plastic foil and/or aluminum foil pouches which are sealed. Another drying step and filling of the pouch with an inert gas (like nitrogen or argon gas), before heat sealing of the pouch, may also be carried out.

In the next step the devices closed into the packages, are sterilized with γ-radiation, using a standard dose of radiation (e.g., 2.5–3.5 MRad). If gas sterilization (like ethylene oxide) or plasma sterilization, will be used, the devices must be sterilized before closing the package.

Naturally, the above-mentioned steps of manufacturing devices of the present invention may further include additional steps, such as for quality control purposes. These additional steps may include visual or other types of inspections during or between the various steps, as well as final product inspection including chemical and/or physical testing and characterization steps, as well as other quality control testing.

The following examples describe some important embodiments of the invention.

EXAMPLE 1

Bioactive glass 13-93 was manufactured according to PCT Pat. Appl. WO 96/21628, the entire disclosure of which is incorporated herein by way of this reference.

Raw materials ($Na_2CO_3$, $CaCO_3$, $CaHPO_4*2H_2O$, $SiO_2$, MgO, $K_2CO_3$) were measured as powders, mixed and melted in a platinum crucible at 1360° C. for 3+3 hours to form bulk glass. Bulk glass was then used for manufacturing of particles, spherical particles and fibers.

Glass particles

Bulk glass was crushed in an agate (99.9 % $SiO_2$) grinding bowl with agate grinding balls in a planetary mill (Fritch Pelverisette 5, Germany). Agate bowl and balls were used to avoid glass contamination during grinding.

Particles (see FIG. 1) were sieved to the particle fraction 50–125 µm and washed with ethanol.

Spherical glass particles

The grinded and irregularly shaped glass particles were transformed into spherical ones by flame spraying (see M. Brink et al., Bioceramics, 9, 1996, pp. 127–130, the entire disclosure of which is incorporated herein by way of this reference). In the flame spraying process, the glass particles are fed into the spray gun and then sprayed with a carrier gas in the flame, where they melt. The spherical particles are then collected into a container. Pressurized air was used as a carrier gas for the particles. The flame consisted of a mixture of acetylene and oxygen. The particle size distribution used in flame spraying was 50–125 µm. The bioactivity of the glass 13-93 was maintained during and after the sphere manufacturing process.

Figure 4:
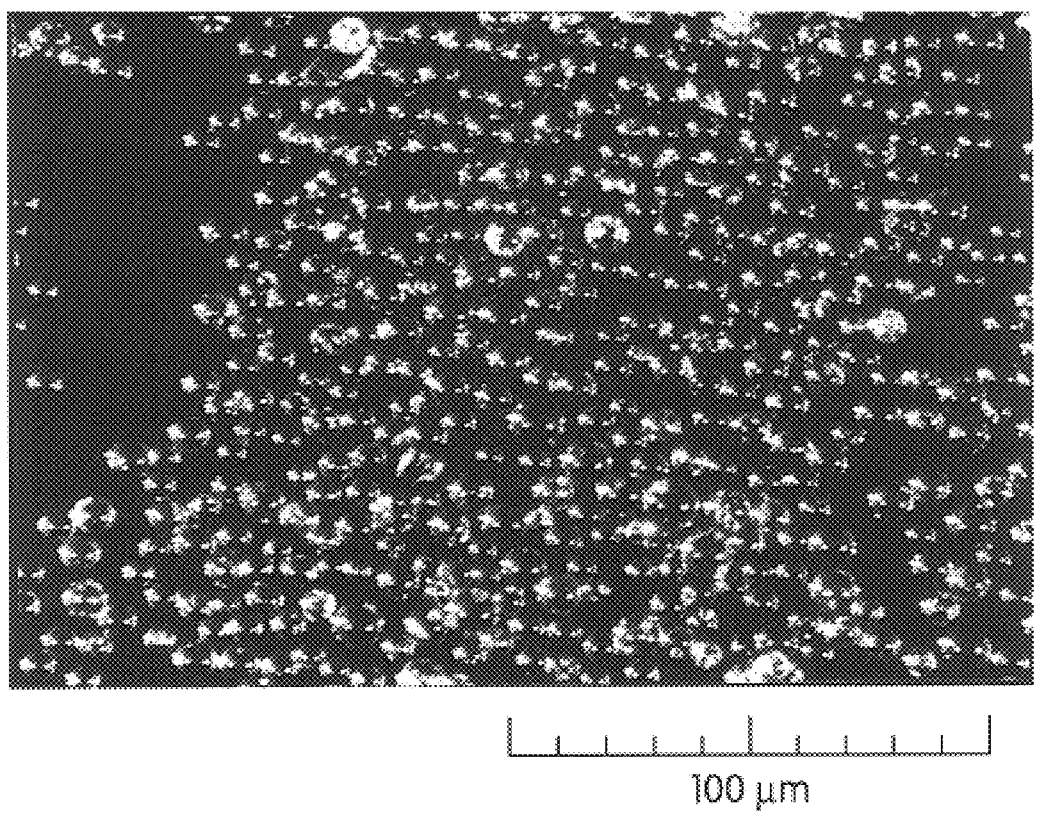
FIG. 4 is a SEM figure of glass BG-13 spheres sieved to a particle fraction of 50–125 μm.

FIG. 4 shows spherical glass particles of 50–125 µm manufactured with the flame spraying process.

Fiber spinning

The continuous glass fibers were manufactured by a melt spinning (drawing) process using bioactive glass 13-93.

Glass particles were heated in a platinum crucible to the temperature where the viscosity range for fiber drawing is achieved (<1000° C., about 30–60 min). A platinum crucible with 4 orifices, approx. diameter 3,6 mm, at the bottom was used. The viscous glass melt formed drops at the crucible orifices. When the drops started to fall they were caught/touched and pulled to form the fibers and attached to the take-up wheel. By varying the spinning velocity the fiber diameter could be modified.

Glass fibers with diameters of about 63 µm and 113 µm were manufactured and their tensile strength and modulus were determined.

The fibers (ten specimens) were tested just after fiber spinning in air at room temperature with a tensile testing machine (Instron 4411, Instron Ltd, England) at a cross head speed of 20 mm/min (standard recommendation: ASTM D 3379-75, Standard Test Method for Young's Modulus for High-Modulus Single-Filament Materials). TABLE 1, below, gives fiber tensile strength and modulus values as recorded.

TABLE 1

| Average diameter (μm) | Average tensile strength (MPa) | Standard deviation | Modulus (Gpa) | Standard deviation |
|---|---|---|---|---|
| 63 | 849 | 204 | 43.2 | 10.2 |
| 113 | 727 | 214 | 44.4 | 7.5 |

EXAMPLE 2
MANUFACTURING OF COMPOSITES OF P(L/DL)LA (70/30) AND BIOACTIVE GLASS (BG) 13-93 PARTICLES

Manufacturing of non-reinforced composite rods

Lactide copolymer powder P(L/DL)LA 70/30 (Resomer® LR 708 (inherent viscosity of 5.5 dl/g, available from Boehringer Ingelheim, Ingelheim am Rhein, Germany) with different weight fractions (from 0 wt. % to 30 wt. %) of glass particles of EXAMPLE 1 were mixed mechanically and poured into a hopper of a single screw extruder (model Gimac TR ø 12/24 B.V.O, of MAC.GI SRL, Castronno, Italy). A nitrogen atmosphere ($N_2$ flow 5 l/min) was supplied to the hopper to avoid contact with the room's air. The rotating screw, together with friction of compression and heating of the outside of the hopper, plasticized the thermoplastic material and pushed the polymer melt-glass powder mixture towards the barrel end and die orifice. Temperatures of the heating zones (from feed zone to die orifice) were 150° C.–160° C.–170° C.–185° C.–205° C. and 221° C. (at the die orifice).

The cylindrical extrudate rods with diameters of 2–8 mm were precooled in a $N_2$ atmosphere and placed on a transportation band for cooling to room temperature. Mechanical tests (bending) were done at room temperature for extruded rods (diameter of 3.5 mm) with different weight fractions of bioactive glass particles (using the testing machine designated Instron 4411, available from Instron Ltd, England). Bending strength decreased from 117 MPa to 112 MPa and bending modulus increased from 2.3 GPa to 3.2 GPa when the portion of glass particles increased from 0 wt. % to 20 wt-%.

Figure 2:
FIG. 2 is a surface SEM figure of an extruded composite rod of P(L/DL)LA containing 17.5±2.5 wt. % of BG-13 glass particles, showing the polymeric skin on glass particles. The distance between scale bars (in the lower part of figure) is 100 μm.

FIG. 2 shows a SEM micrograph of an extruded composite rod with 17.5±2.5 wt. % of glass particles of EXAMPLE 1. Glass particles can be seen clearly below the polymer surface (skin). The composite rods with 0 wt. % of glass particles showed ductile behavior in bending while rods with 20 wt. % or more of glass particles showed brittle behavior in bending.

Manufacturing of self-reinforced composite rods

Extruded P(L/DL)LA and P(L/DL)LA -bioactive glass composite rods were self-reinforced using a solid state die-drawing process.

Figure 7:
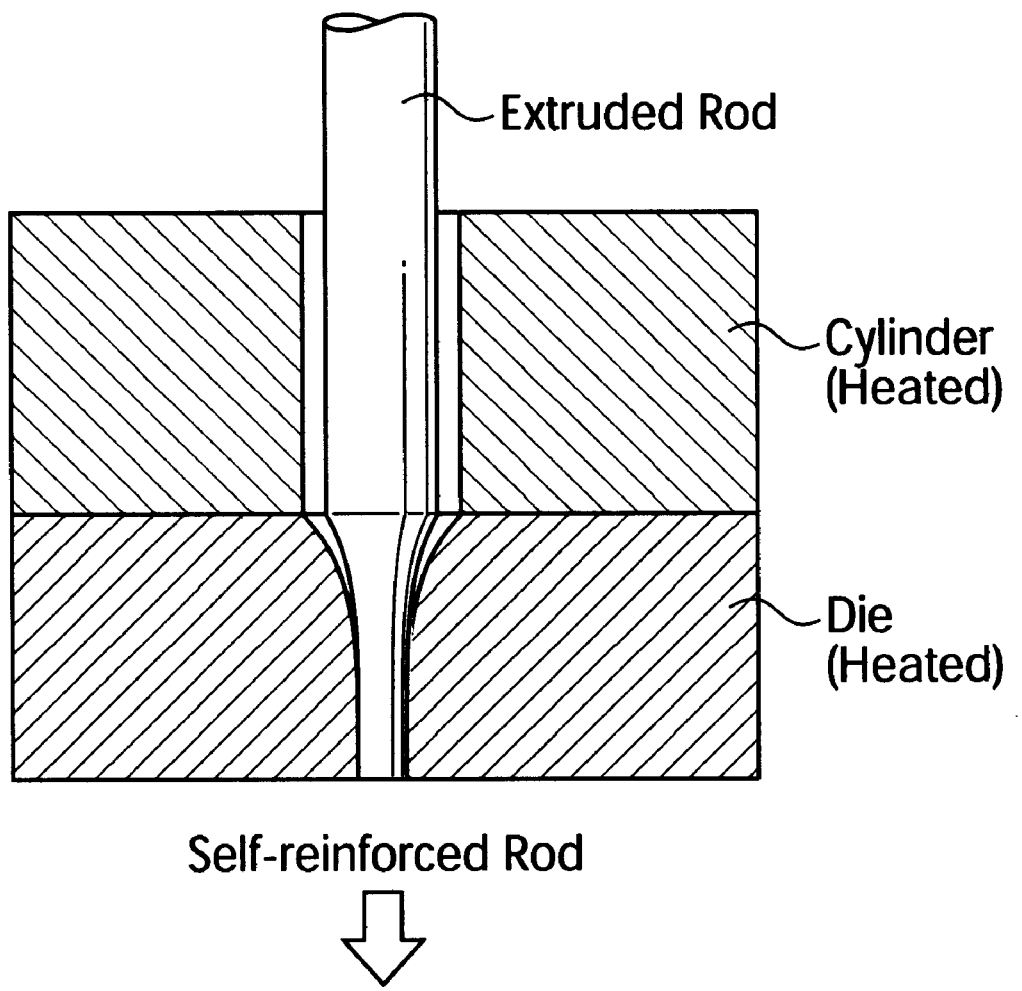
FIG. 7 is a schematic figure of the arrangement of the solid state die-drawing process.

FIG. 7 shows schematically the arrangement of the solid state die-drawing process.

For optimum strength values the different draw temperatures and draw ratios were studied. Drawing temperatures for the pure P(L/DL)LA rods were 70–75° C. and for the P(L/DL)LA rods containing bioactive glass (BG-13) particles they were 85–95° C. Draw ratios of 2–7 were studied. The drawing speed was 10 mm/min. A tensile testing machine designated JJ T5003, available from Lloyd Instruments Ltd, England, was used for drawing the rods fixed at both ends to clamps of that drawing machine.

Figure 3:
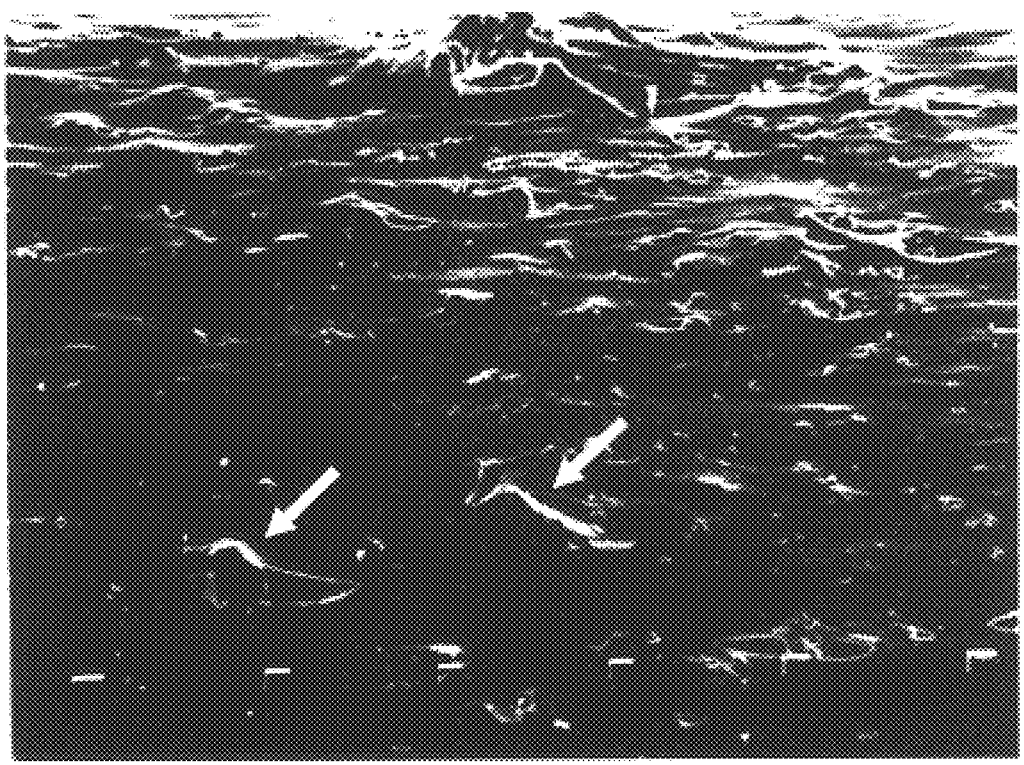
FIG. 3 is a surface SEM figure of a rod of FIG. 2 after the rod has been self-reinforced by solid state drawing to a draw ratio of 3.3. White arrows show two glass particles inside of open pores on the outer surface of the rod.

FIG. 3 shows a SEM figure of the surface of a self-reinforced P(L/DL)LA composite rod containing 20 wt. % of glass particles (draw ratio 3.3). Several spindle-shaped open pores are seen on the surface of the composite rod, and inside of every pore is a glass particle. The polymer skin above the glass particles, which are inside of surface pores, has ruptured during self-reinforcing (drawing) and free particle surfaces are exposed (two such particles are marked with white arrows). TABLE 3 shows the strength and modulus values for some of the studied self-reinforced ("SR") P(LIDL)LA composites containing the BG-13 particles.

TABLE 3

Strength and modulus values of P(L/DL)LA, SR-P(L/DL)LA and their composites with bioactive glass particles.

| Sample No. | Material | Bending strength (MPa) | Bending modulus (Gpa) | Draw ratio |
|---|---|---|---|---|
| (1) | P(L/DL)LA | 117 | 2.3 | — |
| (2) | P(L/DL)LA composites: | | | |
| (2)(a) | 10 wt. % of glass 13–93 particles | 92 | 2.4 | — |
| (2)(b) | 25 wt - % of glass 13–93 particles | 98 | 3.7 | — |
| (3) | SR-P(L/DL)LA composites: | | | |
| (3)(a) | 0 wt - % of glass 13–93 particles | 178 | 3.7 | 4.4 |
| (3)(b) | 10 wt - % of glass 13–93 particles | 160 | 3.7 | 4.2 |
| (3)(c) | 20 wt - % of glass 13–93 particles | 139 | 3.3 | 4.7 |

Samples 1 and 3a–3c were ductile in bending. Samples 2a–2b broke in bending, with a brittle mode.

EXAMPLE 3
MANUFACTURING OF COMPOSITES OF P(L/DL)LA (70/30) AND BIOACTIVE GLASS 13-93 SPHERES

Manufacturing of non-reinforced composite rods

Lactide copolymer powder P(L/DL)LA 70/30 ( Resomer® LR 708 (inherent viscosity of 5.5 dl/g, available from Boehringer Ingelheim, Ingelheim am Rhein, Germany) with different weight fractions (from 0 wt. % to 30 wt. %) of glass spheres of EXAMPLE 1 were mixed mechanically and poured into a hopper of a single screw extruder (model Gimac TR ø 12/24 B.V.O, of MAC.GI SRL, Castronno, Italy). A nitrogen atmosphere ($N_2$ flow 5 /min) was introduced in the hopper to avoid contact with the room's air. The rotating screw, together with friction of compression and heating of the hopper's outer surface, plasticized the thermoplastic material and pushed the polymer melt-glass powder mixture towards the barrel end and die orifice. Temperatures of the heating zones (from feed zone to die orifice) were 150° C.–160° C.–170° C.–185° C.–205° C. and 221° C. (at the die's orifice).

The cylindrical extrudate rods with diameters 2–8 mm were precooled in a $N_2$ atmosphere and placed onto a transportation band for cooling to room temperature. Mechanical tests (bending) were done at room temperature for extruded rods (diameter of 3.5 mm) with different weight fractions of bioactive glass spheres (using the testing machine Instron 4411, Instron Ltd, England). Bending strength decreased from 125 MPa to 115 MPa and bending modulus increased from 2.2 GPa to 3.4 GPa when the portion of glass particles increased from 0 wt. % to 20 wt. %.

Figure 5:
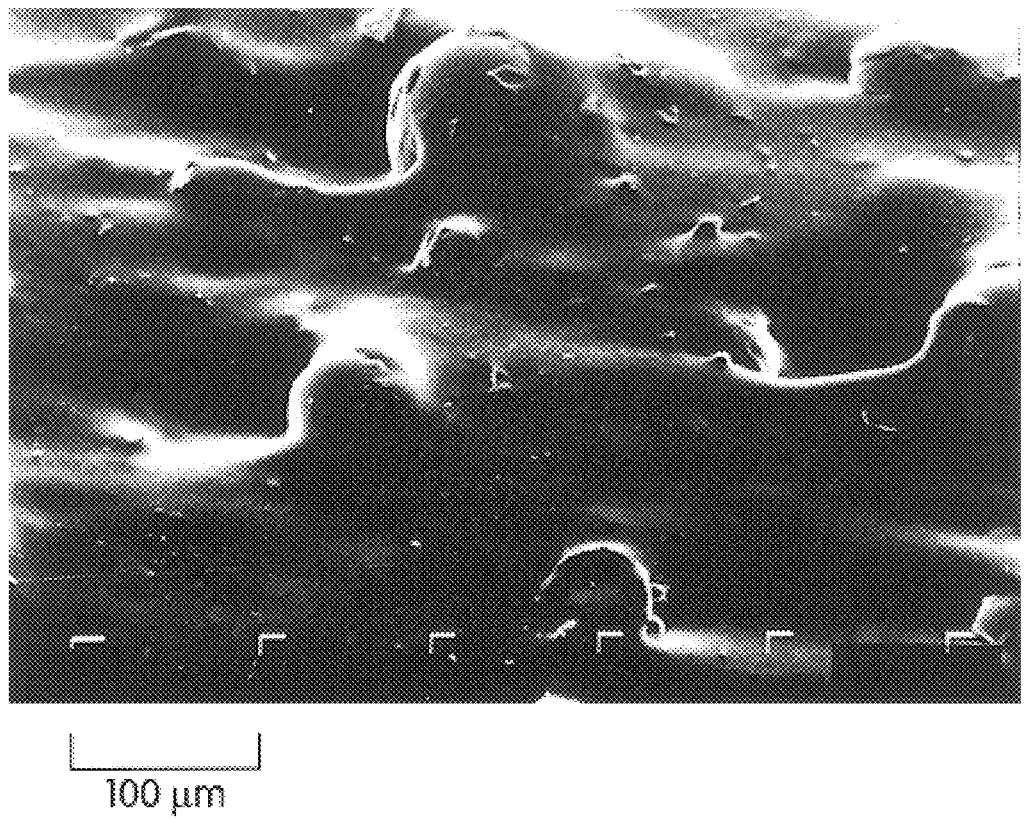
FIG. 5 is a surface SEM figure of an extruded P(L/DL)LA composite rod containing 17.5±2.5 wt. % of BG-13 glass spheres, showing the polymeric skin on glass spheres.

FIG. 5 shows a SEM micrograph of an extruded composite rod containing 17.5±2.5 wt. % of glass spheres of EXAMPLE 1. Glass spheres can be seen clearly below the polymer surface (skin). The composite rods with 0 wt. % of glass spheres showed ductile behavior in bending, while rods with 20 wt. % or more of glass spheres showed brittle behavior in bending.

Manufacturing of self-reinforced composite rods

Extruded P(L/DL)LA and P(L/DL)LA composite rods containing bioactive glass spheres were self-reinforced ("SR") by a solid state die-drawing process.

FIG. 7 shows schematically the arrangement of the solid state die-drawing process. For optimum strength values the different draw temperatures and draw ratios were studied.

Drawing temperatures for pure P(L/DL)LA rods were 70–75° C. and for the P(L/DL)LA rods containing bioactive glass spheres they were 85–95° C. Draw ratios of 2–7 were studied. The drawing speed was 10 mm/min. The instrument designated JJ T5003, Lloyd Instruments Ltd, England, was used for the drawing process.

Figure 6:
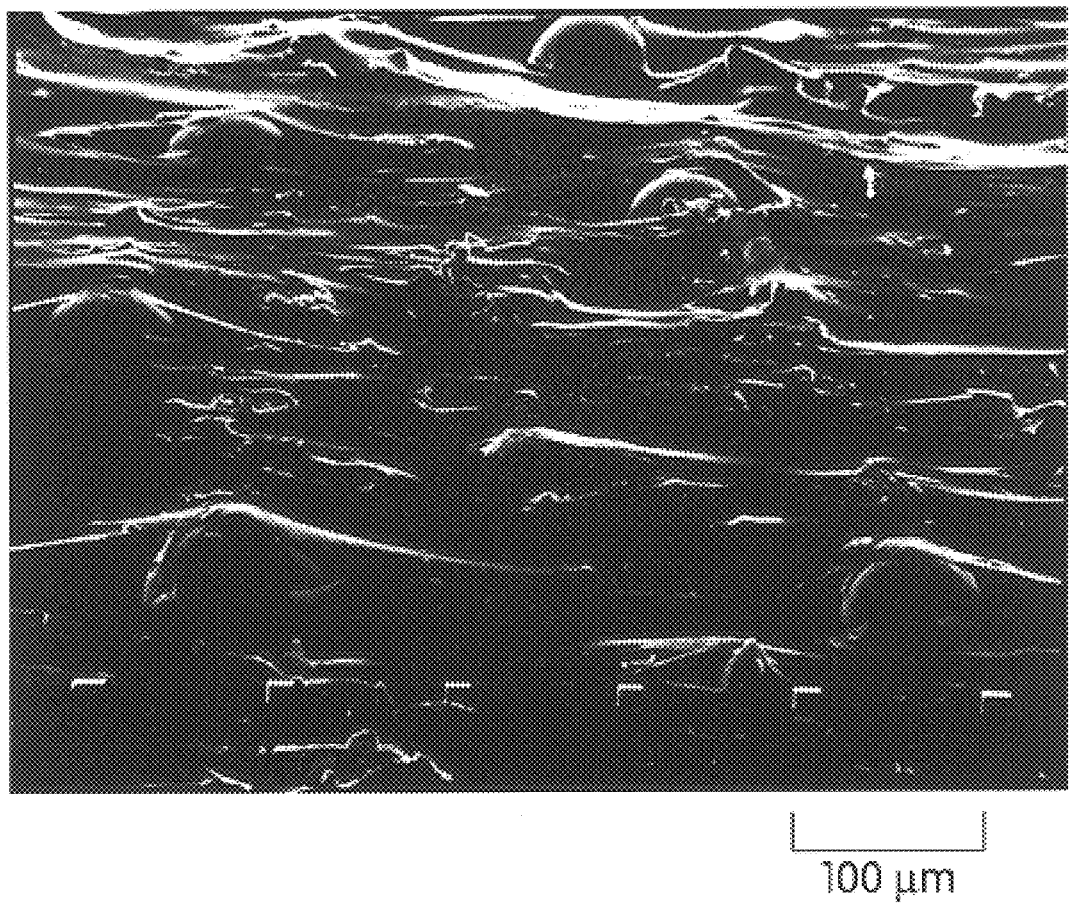
FIG. 6 is a surface SEM figure of a rod of FIG. 5 after the rod had been self-reinforced by solid state drawing to a draw ratio of 3.6.

FIG. 6 shows a SEM figure of the surface of a self-reinforced P(L/DL)LA composite rod containing 20 wt. % of glass spheres (using a draw ratio of 3.3). Several spindle-shaped open pores are seen on the surface of the composite rod, and inside of every pore is a glass sphere. The polymer skin above the glass spheres (which are inside of surface pores) has ruptured during self-reinforcing (drawing) and free sphere surfaces are exposed.

Bending strengths of P(L/DL)LA-bioactive glass sphere composite rods increased 20–50% as a consequence of self-reinforcing. For example, the bending strength of P(L/DL)LA containing 20 wt. % of BG-13 spheres increased from 117 MPa to 156 MPa after self-reinforcing by drawing (using a draw ratio of 3.9). All the materials were transformed from brittle to ductile ones as a consequence of self-reinforcing, even when porosity was developed in those materials.

Figure 8A:
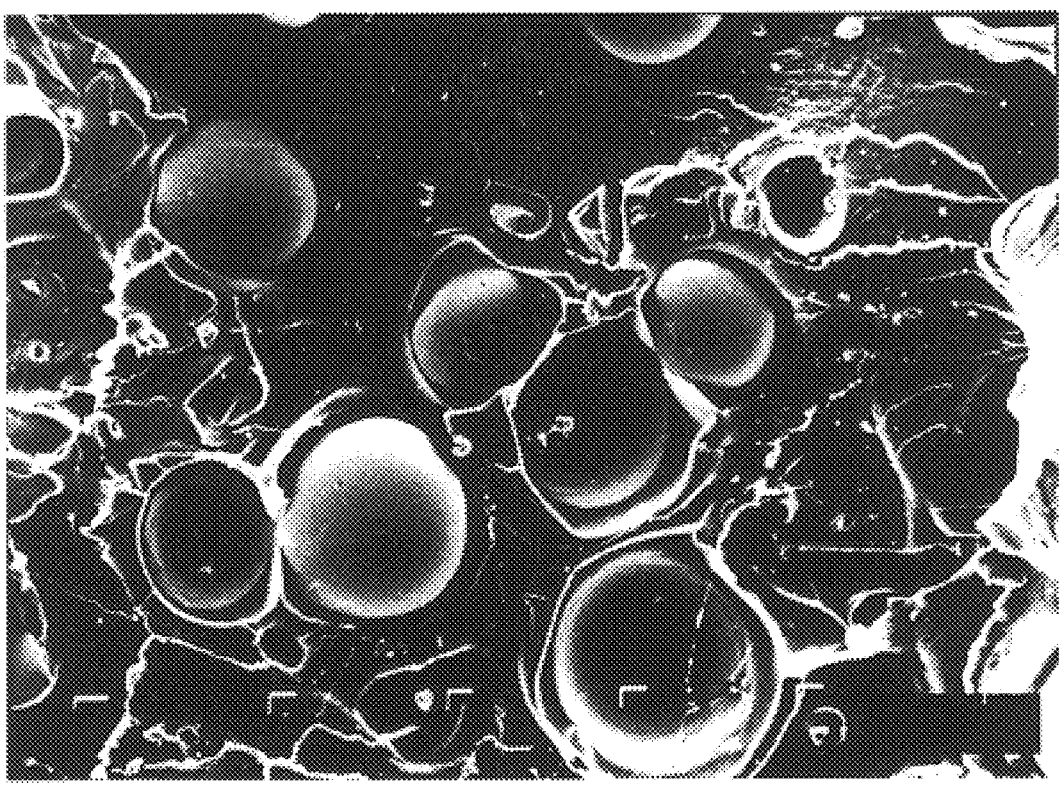
FIG. 8A is a SEM figure of internal structure of an extruded P(L/DL)LA composite rod containing 17.5±2.5 wt. % of BG-13 glass spheres.
Figure 8B:
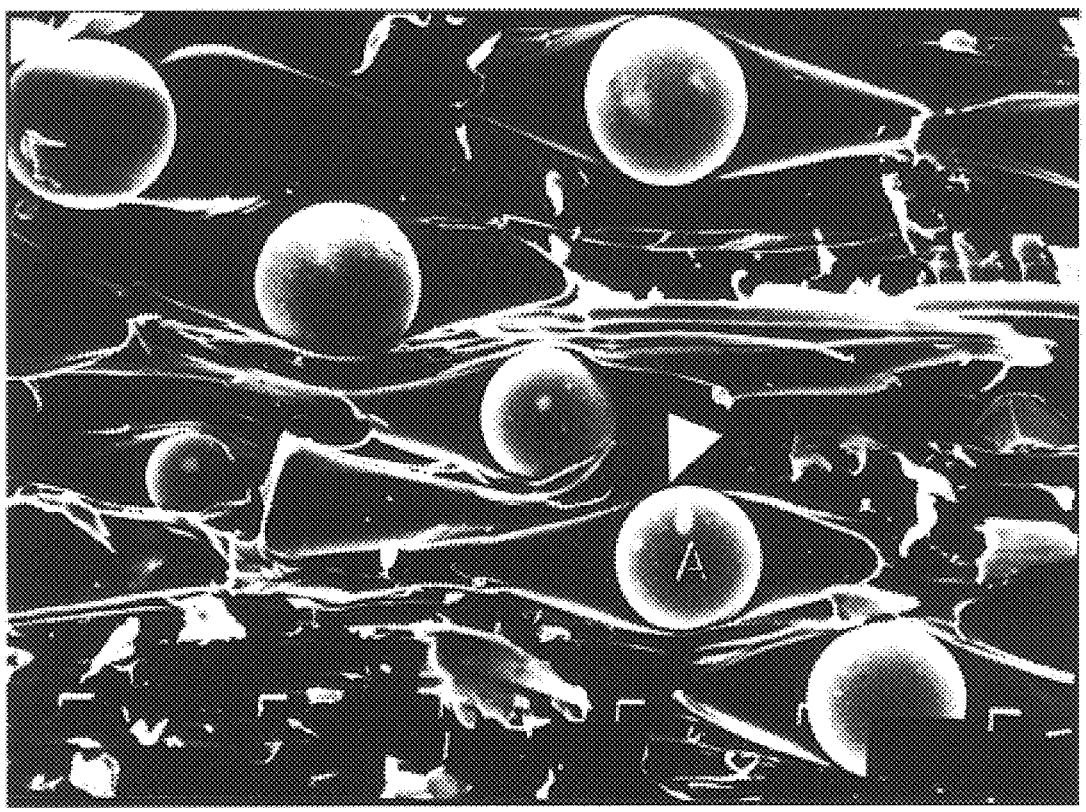
FIG. 8B is a SEM figure of internal structure of the corresponding composite rod after self-reinforcing by drawing (draw ratio 3.6).

FIG. 8A shows a SEM figure of the internal structure of an extruded composite rod of P(L/DL)LA containing 17.5±2.5 wt. % of BG-13 glass spheres. The rod was split mechanically with a sharp knife and the exposed internal structure was studied by SEM. The glass spheres are in an intimate contact with the polymer matrix, which as such is practically non-porous. FIG. 8B shows the internal structure of the corresponding composite rod after self-reinforcing. The self-reinforced rod was split longitudinally and the exposed internal structure was studied by SEM. The draw direction is horizontal in FIG. 8 B. Longitudinal orientation and self-reinforcing have created spindle-shaped pores around the glass spheres. A white arrow head shows a point where one pore has opened into another (second) pore so that the pores are connected with each other and a glass sphere (A) is exposed partially into the second pore that is located by the sphere's original pore.

All the materials which were brittle in bending before self-reinforcing were ductile in bending after self-reinforcing.

EXAMPLE 4

Hydrolysis of non-reinforced and self-reinforced polymers and composites

In hydrolytic conditions in simulated body fluid, bioactive glasses dissolve partially (starting from the glass surface) and calcium phosphate or carbonated hydroxyapatite layer precipitations develop on the glass surface (see, e.g., M. Brink "Bioactive Glasses with a Large Working Range" Doctoral Thesis Åbo Akademi University, Turku, Finland, 1997, and M. Marcolongo et al. J. Biomed. Mater. Res. 39 (1998) 161, the entire disclosures of each of which are incorporated herein by way of this reference). The formation of such precipitations is an indication of bioactive behavior of the bioabsorbable composite, and such precipitations are advantageous especially in bone surgery because they enhance new bone growth in close contact with the implant surface.

In this example, we studied the bioactive behavior of materials of the invention in comparison to the behavior of prior art materials by examining the degradation of polymeric and composite samples in simulated body fluid (SBF) (see T. Kokubo et al. in Bioceramics, Vol. 2, ed. G. Heimke, Deutsche Keramische Gesellschaft e.V., Cologne, Germany, 1990 pp. 235–242, the entire disclosure of which is incorporated herein by way of this reference).

Cylindrical samples (diameter 3 mm and length 15 mm) were placed into plastic pots filled with 200 ml of SBF. Sample solutions were kept at 37° C. for one week. Surface reactions were examined from dried and carbon coated sample surfaces with SEM.

The following samples were examined:
(A) Extruded P(L/DL)LA (70/30) rod;
(B) Self-reinforced ("SR" as used herein) P(L/DL)LA (70/30) rod (draw ratio of 3.3);
(C) Extruded composite rod: P(L/DL)LA (70/30) with 20 wt. % of glass BG-13 particles
(D) Extruded composite rod: P(L/DL)LA (70/30) with 20 wt. % of glass BG-13 spheres
(E) Material C as self-reinforced (draw ratio=3.3)
(F) Material D as self-reinforced (draw ratio=3.3)

Rod surface reactions were examined with SEM after 4 weeks immersion of samples in SBF. Results are given in TABLE 4.

TABLE 4

| Sample | Surface Reactions |
| --- | --- |
| A | No significant changes |
| B | No significant changes |
| C | No significant changes |
| D | No significant changes |
| E | Calcium phosphate precipitations around pores |
| F | Calcium phosphate precipitations around pores |

This example demonstrated that only self-reinforced, porous, bioabsorbable polymer rods (samples E and F) with bioactive glass particles and spheres, exhibited bioactive behavior after four weeks of hydrolysis in the SBF. The evident reason for this is that the glass particles or spheres are exposed to the sample surface via the open surface pores only, after self-reinforcing has broken the skin over the particles and opened the pores to the sample surface.

EXAMPLE 5

After showing in the above example the bioactivity of the materials of the invention in vitro, this example demonstrated the bioactivity of the composites of the invention in vivo, after implantation in a bony environment.

Polymeric composite rods containing a bioactive glass particle filler and all-polymer control specimens were implanted in rabbit femurs. Based on in vitro experiments, we assumed that the self-reinforced composite rods would form a bond to bone tissue, providing early fixation between the implant material and bone. Interfacial bond strengths between the implant materials and bone tissue were measured, and the mechanism of bone tissue incorporation into the composite material was investigated.

Cylindrical samples with diameter of 3 mm and length of 15 mm were machined from both the extruded and the additionally self-reinforced materials designated as A through F in EXAMPLE 4. The implants were sterilized using gamma radiation with a dose of 2.5 Mrad. One composite and one control polymer or composite specimen were implanted bilaterally into 3 mm diameter drill holes in the distal femur of eight rabbits, using aseptic techniques. The rabbits were euthanized by injection of nembutal six weeks after the implantation, and each femur was harvested. The bones were cross sectioned in the region of the implant using saline as a cutting fluid, while maintaining the moisture in the samples. The implant/bone composite was then sectioned transverse to the long axis of the implant, leaving half of the implant/bone section for mechanical testing and the remaining half for histology. The implant was pushed out of bone and the interfacial bond strength between polymer or composite sample and bone was calculated using test arrangements described in Marcolongo et al., J. Biomed. Mater. Res. 39 (1998) pp. 161–170, the entire disclosure of which is incorporated herein by way of this reference.

TABLE 5 gives interfacial bond strengths between samples A–F and bone.

TABLE 5

| Sample | Interfacial bond strength |
|--------|---------------------------|
| A | 4 ± 0.4N |
| B | 4.6 ± 0.5N |
| C | 4.5 ± 0.6N |
| D | 4.7 ± 0.4N |
| E | 8.8 ± 0.6N |
| F | 9.0 ± 0.8N |

TABLE 5 shows that the self-reinforced composite rods E and F, which had pores open to the surface of the implant with bioactive glass particles in those pores, exhibited about two times higher interfacial bond strengths in comparison to polymer samples A and B and to composite samples C and D, which had a thin polymer skin covering bioactive glass particles or spheres.

Histologically, the surfaces of SR-composites (samples E and F) showed close apposition to bone tissue at six weeks. Most of the composite surfaces had direct bone contact. Only about 20% of the interface had thin fibrous tissue between the composite and bone.

The respective interfaces between the sample and bone in samples A and B were mostly interposed by fibrous tissue, and in samples C and D more than half of their respective interfaces were fibrous.

This in vivo study showed that self-reinforced composite samples E and F (containing pores open to the surface of the implant and bioactive glass particles in those pores) enhanced new bone formation significantly better than polymeric samples A and B (which had no bioactive ceramic filler) and composite samples C and D, each having a polymeric skin covering bioactive glass particles and spheres.

EXAMPLE 6

This example demonstrated the effect of bioactive implants of the invention on healing of bone fractures (osteotomies).

Pellets of copolymer material comprising about 80 mol-% of L-lactide and about 20 mol-% of glycolide (PLGA) were supplied by PURAC Biochem bv, Gorinchem, Holland. The pellets had an inherent viscosity of about 5.9 dl/g and a molecular weight $M_w$ of about 336,000. The inherent viscosity was measured at 25° C. using 100 mg polymer per 100 ml of chloroform.

Thermoplastic, bioabsorbable pseudo-polyaminoacid poly (DTH carbonate) (PDTHC) ($M_w$=200,000) was synthesized according to S. I. Ertel and J. Kohn, J. Biomed. Mater. Res. 28 (1994) 919–930 and F. H. Silver et al., J. Long-Term Effects Med. Implants 1 (1992) 329–346, the entire disclosure of which is incorporated herein by way of this reference.

Thermoplastic, bioabsorbable polyorthoester (POE) ($M_w$=80,000) was synthesized from diketene acetal, diols of trans-cyclohexane dimethanol and 1,6 -hexanediol (60/40 ratio of diols) according to Daniels, A. U. et al., Trans. Soc. Biomater. 12 (1989) 235 and Daniels, A. U. et al. Trans. Soc. Biomater. 12 (1989) 74, the entire disclosure of which is incorporated herein by way of this reference.

Thermoplastic, bioabsorbable polyanhydride (PAH) ($M_w$=20,000) was synthesized from 1,3 bis (p-carboxyphenoxy) propane and sebacic acid according to U.S. Pat. No. 5,618,563, Example 1, the entire disclosure of which patent is incorporated herein by way of this reference.

Poly-L-lactide (PLLA) ($M_w$=700,000) was supplied by PURAC biochem bv, Gorinchem, Holland. Each polymer powder or granulate, PLGA, PDTHC, POE, PAH and PLLA was mixed mechanically with 25 wt. % of BG-13 spheres of EXAMPLE 1 and extruded to cylindrical bars with diameters of 2–8 mm, using a single screw extruder (Axon BX-15, Axon Plastikmaskiner, Sweden). The composite rods were oriented and/or self-reinforced uniaxially by drawing them through a heated die at a temperature (T) of 20 to 40° C. above the $T_g$ of the corresponding polymer. Draw ratios between 2–3 were studied for POE and PAH and draw ratios of 2–6 for PLGA, PDTHC and PLLA. SEM figures of composite rod surfaces showed analogous open surface pores with BG-13 spheres therein, as in the self-reinforced P(L/DL)LA rods of EXAMPLE 3.

Composite rods with the draw ratio of 3 and diameter of 2.0–2.1 mm were selected for animal experiments. Corresponding oriented and/or self-reinforced PLGA, PDTHC, POE, PAH and PLLA rods (manufactured from the same raw polymer materials by extrusion and solid state drawing to the draw ratio of 3) were used as control rods. All the rods were sterilized with gamma radiation (2.5 Mrad dose).

For each type of (glass particle-containing) composite rods and the control rods (based on PLGA, PDTHC, POE, PAH and PLLA polymers) an animal study was done to study bioactive behavior of the rods in vivo. In each case, the bioactive BG-13 containing composite rods and control rods were used in fixation of osteotomies of distal metaphysis of femurs in rats, in the following way. The right knee of a Wistar rat was shaved and sterilized with Neo-Amisept®. Wistar rats of both sexes, 12 weeks old and weighing 250–350 g were used. The rats received $CO_2$ by inhalation, for induction, and anaesthesia was continued with 0.1 mg/300 g medetomidine (Domitor™, Lääkefarmos, Turku, Finland) and 3 mg/300 g ketalar (Ketalar™, Parke-Davis, Barcelona, Spain) by subcutaneous injections. An incision was made through the medial side to open the knee. The patella was dislocated laterally and the distal end of the femur was exposed. A 2 mm drill hole was made through the intercondylar space. An osteotomy was done through the metaphysis leaving the posterior cortex intact to serve as a hinge. A self-reinforced BG-13 containing composite rod or a self-reinforced control rod, having diameter of 2.0–2.1 mm and length of 15 mm, was introduced through the hole to fix the osteotomy. The wounds were closed with 4-0 USP PGA sutures (Dexon®, Davis & Geck, USA).

Postoperatively, the rats were returned into their cages, where they recovered from anaesthesia. They were given a regular normal laboratory animal diet. They were followed-up for 1, 3, 6 and 12 weeks. Each follow-up group comprised 4 rats having the composite rods containing the BG-13 particles and 4 control rod rats. After sacrifice, both femurs were exarticulated. Immediate postoperative plain radiographs (anteroposterior and lateral views) were taken of both femora (taget tube distance 100 cm, exposure factors 40 kV, 5 mA and 0.03 s). The healing of the osteotomies was evaluated radiologically, histologically and with mechanical testing by shearing the fixed bone part along the osteotomy plane. The mechanical tests were done according to M. Manninen and T. Pohjonen, Biomaterials, 14 (1993) 305–312, the entire disclosure of which is incorporated herein by way of this reference.

In order to eliminate the effect of the fixation rod on the shear strength of osteotomy, the in vivo shear strength retention of the BG-13 composite rods and control rods was studied in the following way. BG-composite rods and control rods 15 mm long and 2 mm in diameter were used. The rods were sterilized by gamma radiation. The rod packages were opened just before tests started. Wistar rats of both sexes, 12 weeks old and weighing 250–350 g, were operated on. The rats received $CO_2$ by inhalation, for induction, and anaesthesia was continued with 0.1 mg/300 g medetomidine (Domitor™, Lääkefarmos, Turku, Finland) and 3 mg/300 g ketalar (Ketalar™, Parke-Davis, Barcelona, Spain) by subcutaneous injections. Four BG-13 composite rods or four control rods were implanted in the dorsal subcutaneous tissue of 32 rats, through 4 separate wounds. The wounds were closed with a 4-0 USP PGA sutures (Dexon®, Davis+Geck, USA).

Postoperatively, the rats were returned into their cages, where they recovered from anaesthesia. They were given a regular normal laboratory animal diet. They were followed-up for 1, 3, 6 and 12 weeks. After sacrifice, the rods were removed from the rats, and immediately after removal stored in saline. The shear strength tests were made within 24 h after death and immediately after removal from saline according to M. Manninen and T. Pohjonen, Biomaterials, 14 (1993) 305–312.

The effect of the fixation rod on the shear load carrying capacity of the healing osteotomy at each follow-up period was eliminated by reducing from the total shear load carrying capacity of the healing osteotomy and fixation rod system the shear load carrying capacity of the fixation pin (which value was determined from shear strength measurements of corresponding pins implanted subcutaneously). After 3 and 6 weeks' follow-up periods, radiological and histological examination showed a qualitatively more intense new bone formation in the drill channel and in the osteotomy area of femurs fixed with BG-13 composite rods than in femurs fixed with control rods.

Shear breaking test of osteotomies at the 1 week follow-up period showed practically the same shear strength values for the osteotomies fixed with BG-13 composite rods as for those fixed with control rods. However, at the 3 week follow-up period, the osteotomies fixed with BG-13 composite rods exhibited ca. 20±5% higher shear strength, at 6 weeks follow-up 25±5% higher shear strength and at 12 weeks follow-up 15±5% higher shear strength than the osteotomies fixed with control rods.

After 1 and 3 weeks follow-up, there were no obvious differences between the new bone formation in animals whose osteotomies were fixed with the various BG-13 composite rods, but after 6 and 12 weeks follow-up (based on radiological and histological examination) the new bone formation seemed to be most intense in PDTHC/BG-13 composite rod group and the intensity in the other BG-13 composite rods was smaller in the order: PLLA, POE, PLGA and PAH-group.

This experiment showed that BG-13 composite rods enhanced early bone formation and fracture healing better than the control rods.

EXAMPLE 7

Glass fibers (with diameter 113 $\mu$m) of EXAMPLE 1 were coated with PLGA (described in EXAMPLE 6) by drawing a bundle of 20 continuous fibers through the polymer melt and by cooling the polymer-impregnated fiber bundle in air. The amount of glass fibers was 50 wt. % in the impregnated bundle. The bundle was cut to 3 mm long granules and these were mixed mechanically with pure PLGA powder so that the amount of glass fibers was 25 wt. % in the mixture. The mixture was melt extruded and self-reinforced into rods with diameter of 2 mm, using the procedure described in EXAMPLE 6 (the draw ratio of solid state drawing was 3.4).

SEM examination of rod surfaces showed that glass fibers had broken during extrusion and solid state drawing to the lengths mainly between 150 $\mu$m –1.5 mm. The fibers were oriented strongly with their long axes in the drawing direction and spindle shaped surface pores, including fibers, were seen. Bioactivity of extruded and self-reinforced rods (diam. 2 mm, length 20 mm) was studied in vitro in simulated body fluid (SBF) according to EXAMPLE 4. After 2 weeks immersion of samples in SBF, calcium phosphate precipitations were seen on self-reinforced rods around pores while the extruded rods (not self-reinforced) exhibited no significant changes. Thus, this example demonstrated that only self-reinforced porous, bioabsorbable polymer rods with bioactive glass fibers, exhibited bioactive behavior after two weeks' hydrolysis. The evident reason for this is that the glass fibers are exposed to the sample surface via the open surface pores only after self-reinforcing has broken the skin over the fibers, thereby opening the pores to the sample surface.

What is claimed is:

1. A bioactive, bioabsorbable surgical composite material comprising:
    a bioabsorbable polymer matrix which is oriented, said matrix having an outer surface and containing a plurality of pores, wherein at least some of said pores open at the surface of said matrix; and bioabsorbable or bioactive particles dispersed into the polymer matrix, said particles being comprised of glass or ceramic, wherein said particles extend at least partially into said pores.

2. A composite material according to claim 1, wherein at least some of said particles extend through the pores open at the surface of the matrix.

3. A composite material according to claim 1, wherein each of the pores in the matrix is not in contact with any of the other pores.

4. A composite material according to claim 1, wherein at least part of at least one of said pores is connected with at least one of the other of said pores.

5. A composite material according to claim 1, wherein said matrix is self-reinforced.

6. A bioactive, bioabsorbable surgical composite material, comprising:

a bioabsorbable polymer matrix which is oriented, said matrix having an outer surface and containing a plurality of pores, wherein at least some of said pores open at the surface of said matrix; and bioabsorbable or bioactive fibers dispersed into the polymer matrix, wherein said fibers extend at least partially into said pores.

7. A composite material according to claim 6, wherein at least some of said fibers extend through the pores open at the surface of the matrix.

8. A composite material according to claim 6, wherein each of the pores in the matrix is not in contact with any of the other pores.

9. A composite material according to claim 6, wherein at least part of at least one of said pores is connected with at least one of the other of said pores.

10. A composite material according to claim 6, wherein said matrix is self- reinforced.

* * * * *

UNITED STATES PATENT AND TRADEMARK OFFICE
CERTIFICATE OF CORRECTION

PATENT NO. : 6,406,498 B1
DATED : June 18, 2002
INVENTOR(S) : Törmälä et al.

It is certified that error appears in the above-identified patent and that said Letters Patent is hereby corrected as shown below:

Title page,
Item [54], change "BIOACTIVE, BIOABSORBABLE SURGICAL COMPOSITE MATERIAL" to -- BIOACTIVE, BIOABSORBABLE SURGICAL COMPOSITES AND DEVICES --;

Column 10,
Line 44, change "5/min" to -- 51/min --.

Signed and Sealed this

Eleventh Day of March, 2003

JAMES E. ROGAN
*Director of the United States Patent and Trademark Office*